US006686482B2

(12) United States Patent
Harada et al.

(10) Patent No.: US 6,686,482 B2
(45) Date of Patent: Feb. 3, 2004

(54) PROCESS FOR PREPARING PIPERONAL

(75) Inventors: Katsumasa Harada, Ube (JP); Masashi Shirai, Ube (JP); Koji Shiba, Ube (JP); Toshio Furuya, Ube (JP)

(73) Assignee: Ube Industries, Ltd., Yamaguchi (JP)

( * ) Notice: Subject to any disclaimer, the term of this patent is extended or adjusted under 35 U.S.C. 154(b) by 0 days.

(21) Appl. No.: 10/182,485

(22) PCT Filed: Feb. 2, 2001

(86) PCT No.: PCT/JP01/00739
§ 371 (c)(1), (2), (4) Date: Jul. 30, 2002

(87) PCT Pub. No.: WO01/57016
PCT Pub. Date: Aug. 9, 2001

(65) Prior Publication Data
US 2003/0013897 A1 Jan. 16, 2003

(30) Foreign Application Priority Data
Feb. 2, 2000 (JP) .......................................... 2000-24638

(51) Int. Cl.$^7$ ............................................. C07D 317/54
(52) U.S. Cl. ........................ 549/436; 549/534; 549/446
(58) Field of Search ................................ 549/434, 436, 549/446

(56) References Cited
U.S. PATENT DOCUMENTS
4,190,583 A * 2/1980 Bauer et al. ................ 549/447

FOREIGN PATENT DOCUMENTS

| EP | 0 002 460 A | 6/1979 |
|----|-------------|--------|
| JP | 7-330755 A  | 12/1995 |
| JP | 8-99971 A   | 4/1996 |

* cited by examiner

Primary Examiner—Ba K. Trinh
(74) Attorney, Agent, or Firm—Frishauf, Holtz, Goodman & Chick, P.C.

(57) ABSTRACT

The present invention is to provide a process for producing piperonal which comprises continuous three steps of:

(A) an addition reaction step wherein 1,2-methylenedioxybenzene and glyoxylic acid are reacted to form 3,4-methylenedioxymandelic acid in the presence of a strong acid, (B) an extraction step wherein an organic solvent is then added to a reaction mixture and the mixture is neutralized with a base to extract 3,4-methylenedioxymandelic acid in an organic solvent layer, and separating the organic solvent layer and an aqueous layer, and (C) an oxidation reaction step wherein the aqueous layer is removed and the organic solvent layer is concentrated, and then, nitric acid is added to a concentrate, and the 3,4-methylenedioxymandelic acid and nitric acid are reacted to form piperonal.

15 Claims, No Drawings

PROCESS FOR PREPARING PIPERONAL

This application is a U.S. National Phase Application under 35 U.S.C. 371 of International Application No. PCT/JP01/00739 filed Feb. 2, 2001.

TECHNICAL FIELD

The present invention relates to a process for producing piperonal, more specifically to a process for producing a high quality piperonal with high yield by using 1,2-methylenedioxybenzene as a starting material and without taking 3,4-methylenedioxymandelic acid which is an intermediate in the course of the reaction as a crystal.

BACKGROUND ART

Piperonal is a base material for preparing a heliotrope type perfume and has widely been used as a perfume for general cosmetics, and in addition, it is a useful compound as a starting material for synthesis of medical and agricultural chemicals and a brightener for metal plating.

As a method for producing piperonal, it has been generally known a method of oxidizing 3,4-methylenedioxymandelic acid with nitric acid (for example, P. S. Raman Current Science, 27, 22 (1958), Perfumer & Flavourist, 14, 13 (1989), EP 429316, etc.). Also, it has been known that 3,4-methylenedioxymandelic acid can be produced by reacting 1,2-methylenedioxybenzene and glyoxylic acid in the presence of sulfuric acid, etc. (for example, Japanese Provisional Patent Publication No. 95573/1979, Perfumer & Flavourist, 14, 13 (1989), etc.).

In the method of producing piperonal through 3,4-methylenedioxymandelic acid as mentioned above, the 3,4-methylenedioxymandelic acid formed by the initial reaction (hereinafter referred to as addition reaction) of 1,2-methylenedioxybenzene and glyoxylic acid is insoluble in the reaction system and precipitates as crystals. Thus, after separating the crystals of the 3,4-methylenedioxy-mandelic acid by an operation such as filtration, a subsequent reaction (hereinafter referred to as oxidation reaction) of 3,4-methylenedioxymandelic acid and nitric acid has been carried out. However, operations such as filtration, etc. are complicated, and this method is disadvantageous as an industrial preparation process.

On the other hand, it has been known a process for producing piperonal by carrying out an addition reaction and an oxidation reaction continuously without separating and purifying 3,4-methylenedioxymandelic acid in the course of the operations (Japanese Provisional Patent Publication No. 330755/1995). In this process, a relatively high quality piperonal can be produced with high yield. However, at the time of oxidation reaction, 1,2-methylene-dioxy-4-nitrobenzene is contaminated in crude piperonal in an amount of 0.5 to 1.0% by weight or so. This 1,2-methylenedioxy-4-nitrobenzene is a compound which can be confirmed to be colored with naked eyes even when it is contaminated in piperonal in an amount of several tens ppm or more, and when it is once formed, it is difficult to remove from piperonal by a general purification method such as distillation, recrystallization, activated charcoal treatment, etc. Thus, there is a problem of lowering quality of the product by causing coloring of piperonal.

An object of the present invention is to provide a process which is capable of producing a high quality piperonal with high yield by completely inhibiting formation of 1,2-methylenedioxy-4-nitrobenzene, without taking out 3,4-methylenedioxymandelic acid which is an intermediate in the course of the reaction as a crystal, and carrying out from the above-mentioned addition reaction step to the oxidation reaction step continuously using 1,2-methylenedioxybenzene as a starting material.

DISCLOSURE OF THE INVENTION

The present invention relates to a process for producing piperonal which comprises three steps of:
(A) an addition reaction step wherein 1,2-methylenedioxybenzene and glyoxylic acid are reacted to form 3,4-methyl-enedioxymandelic acid in the presence of a strong acid,
(B) an extraction step wherein thereafter, an organic solvent is then added to a reaction mixture and the mixture is neutralized with a base to extract 3,4-methylenedioxymandelic acid in an organic solvent layer, and separating the organic solvent layer and an aqueous layer, and
(C) an oxidation reaction step wherein the aqueous layer is removed and the organic solvent layer is concentrated, and then, nitric acid is added to a concentrate, and the 3,4-methylenedioxymandelic acid and nitric acid are reacted to form piperonal.

BEST MODE FOR CARRYING OUT THE INVENTION

In the present invention, as mentioned above, the following three steps are continuously carried out without taking out 3,4-methylenedioxymandelic acid which is an intermediate as a crystal in the course of the reaction.
(A) Addition reaction step in which 1,2-methylenedioxybenzene and glyoxylic acid are reacted in the presence of a strong acid to form 3,4-methylenedioxymandelic acid.
(B) Extraction step in which an organic solvent is then added to the reaction mixture, followed by neutralization with a base, whereby extracting 3,4-methylenedioxymandelic acid in an organic solvent layer, to separate the organic solvent layer and an aqueous layer.
(C) Oxidation reaction step in which the aqueous layer is then removed, and after concentrating the organic solvent layer, nitric acid is added to the concentrate whereby 3,4-methylenedioxymandelic acid and nitric acid are reacted to form piperonal.

In the following, the above-mentioned three steps are successively explained.

(A) Addition Reaction Step

The addition reaction step of the present invention is a step of forming 3,4-methylenedioxymandelic acid by reacting 1,2-methylenedioxybenzene and glyoxylic acid in the presence of a strong acid.

As a strong acid to be used in the addition reaction step of the present invention, there may be preferably mentioned inorganic acids such as sulfuric acid, phosphoric acid, etc., more preferably sulfuric acid. Also, as these strong acids, 70% by weight or more of an aqueous solution is preferably used. An amount thereof to be used is preferably 0.50 to 3.00 mole, more preferably 1.00 to 2.50 mole based on 1 mole of 1,2-methylenedioxybenzene.

As the glyoxylic acid to be used in the addition reaction step of the present invention, either of a solid (monohydrate) or 40% by weight or more of an aqueous solution may be used. An amount thereof to be used is preferably 0.8 to 2.0 mole, more preferably 1.0 to 1.5 mole based on 1 mole of 1,2-methylenedioxybenzene.

The addition reaction step of the present invention is carried out in the presence or absence of a reaction solvent. As a solvent to be used, it is not particularly limited so long as it is stable under acidic conditions and does not inhibit the reaction, and there may be mentioned, for example, organic acids such as formic acid, acetic acid, propionic acid, n-butyric acid, i-butyric acid, n-valeric acid, trifluoroacetic acid, dichloroacetic acid, etc.; ethers such as diethyl ether, diisopropyl ether, dibutyl ether, tetrahydrofuran, etc.; ketones such as acetone, 2-butanone, 3-pentanone, 2-pentanone, 4-methyl-2-pentanone, cyclopentanone, cyclohexanone, etc.; carboxylic acid esters such as ethyl formate, isopropyl formate, butyl formate, methyl acetate, ethyl acetate, isopropyl acetate, butyl acetate, methyl propionate, ethyl propionate, isopropyl propionate, butyl propionate, etc.; amides such as N,N-dimethylformamide, 1-methyl-2-pyrrolidone, etc.; ureas such as 1,3-dimethyl-2-imidazolidone, etc.; carbonic esters such as dimethyl carbonate, diethyl carbonate, etc., and preferably ketones are used.

An amount of the above-mentioned reaction solvent to be used is preferably 100 to 2000 ml, more preferably 100 to 1000 ml based on 1 kg of the 1,2-methylenedioxybenzene. These reaction solvents may be used singly or in admixture of two or more.

The addition reaction step of the present invention is carried out, for example, by adding glyoxylic acid and a strong acid to a mixed solution of 1,2-methylenedioxybenzene and a reaction solvent in an atmosphere of an inert gas such as nitrogen or argon, etc., or the like. The reaction temperature at that time is preferably −20 to 10° C., more preferably −10 to 5° C. Also, the reaction is usually carried out under normal pressure, but may be carried out under pressure or a reduced pressure, if necessary.

(B) Extraction Step

The extraction step of the present invention is a step in which, after the addition reaction step, an organic solvent is added to the reaction mixture, and then, neutralizing with a base, thereby 3,4-methylenedioxymandelic acid is extracted with the organic solvent layer, to separate the organic solvent layer and an aqueous layer.

As the organic solvent to be used in the extraction step of the present invention, there may be mentioned ketones such as acetone, 2-butanone, 3-pentanone, 2-pentanone, 4-methyl-2-pentanone, cyclopentanone, cyclohexanone, etc.; organic acid esters such as ethyl formate, isopropyl formate, butyl formate, methyl acetate, ethyl acetate, isopropyl acetate, butyl acetate, methyl propionate, ethyl propionate, isopropyl propionate, butyl propionate, etc.; ethers such as diethyl ether, diisopropyl ether, dibutyl ether, tetrahydrofuran, etc., preferably ketones are used.

An amount of the above-mentioned organic solvent to be used is not particularly limited so long as it is an acid in the extraction step, and for example, it is used in an amount of 1 to 10 kg based on 1 kg of 3,4-methylenedioxymandelic acid.

As the base to be used in the extraction step of the present invention, an aqueous alkali metal hydroxide solution (for example, an aqueous sodium hydroxide solution or an aqueous potassium hydroxide solution, etc.) or an aqueous ammonia is suitably used. As a concentration of the aqueous alkali metal hydroxide solution, 10 to 48% by weight is preferred, and as a concentration of the aqueous ammonia, 5 to 28% by weight is preferred.

An amount of the above-mentioned base to be used is an amount necessary for neutralizing the strong acid used in the addition reaction step, and is preferably 2 equivalents based on 1 equivalent of sulfuric acid.

The extraction step of the present invention is carried out, for example, by a method in which an organic solvent is added to the reaction mixture obtained in the addition reaction step, then the reaction mixture is neutralized with a base preferably at −20 to 50° C., more preferably at −20 to 10° C., thereby extracting 3,4-methyl-enedioxymandelic acid with the organic solvent layer, to separate the organic solvent layer and an aqueous layer, or the like. Incidentally, the extraction operation is carried out preferably at 20 to 100° C., more preferably at 40 to 80° C. Also, the extraction operation is usually carried out under normal pressure, but may be carried out under pressure or reduced pressure, if necessary.

(C) Oxidation Reaction Step

The oxidation reaction step of the present invention is a step in which, after the extraction step, the aqueous layer is removed and the organic solvent layer is concentrated, and then, nitric acid is added to the concentrate whereby reacting 3,4-methylenedioxymandelic acid and nitric acid to form piperonal.

The nitric acid to be used in the oxidation step of the present invention is preferably a 5 to 70% by weight aqueous solution. An amount thereof is preferably 0.5 to 1.0 mole, more preferably 0.55 to 0.8 mole based on 1 mole of 1,2-methylenedioxybenzene to be charged.

In the oxidation reaction step of the present invention, depending on necessity, after concentrating an organic solvent layer, a reaction solvent is newly added to react 3,4-methylenedioxymandelic acid and nitric acid.

As the above-mentioned reaction solvent, there may be mentioned, for example, aromatic hydrocarbons such as toluene, xylene, ethylbenzene, etc.; halogenated aromatic hydrocarbons such as chlorobenzene, etc.; ketones such as acetone, 2-butanone, 3-pentanone, 2-pentanone, 4-methyl-2-pentanone, cyclopentanone, and cyclohexanone; halogenated aliphatic hydrocarbons such as methylene chloride, chloroform, carbon tetrachloride, dichloroethane, dibromoethane, etc.; ethers such as diethyl ether, diisopropyl ether, dibutyl ether, tetrahydrofuran, etc., preferably aromatic hydrocarbons and ketones are used.

An amount of the above-mentioned reaction solvent is preferably 1000 to 8000 ml, more preferably 1500 to 5000 ml based on 1 kg of the 1,2-methylenedioxybenzene. These reaction solvents may be used alone or in admixture of two or more kinds.

Also, if necessary, water may be newly added. An amount thereof to be used is not particularly limited so long as it can control a nitric acid concentration in the reaction mixture preferably 5 to 50% by weight, more preferably 5 to 20% by weight.

The oxidation reaction step of the present invention is carried out, for example, by a method in which an aqueous layer is removed from a separated solution obtained in the extraction step, and after concentrating the organic solvent layer, nitric acid is added in an atmosphere of an inert gas such as nitrogen or argon, etc., and the like. The reaction temperature at that time is preferably 5 to 100° C., more preferably 15 to 80° C. Also, the reaction is generally carried out at normal pressure, and if necessary, it may be carried out under pressure or under reduced pressure.

The resulting final product (piperonal) is extracted, for example, by a suitable solvent after neutralization by addition of a suitable amount of a base, and separated and purified by a conventional means such as column chromatography, distillation, recrystallization and the like.

Incidentally, the organic solvent removed in the concentration operation in the oxidation reaction step or a reaction solvent removed at the time of obtaining a final product may be recovered and used again in the above-mentioned addition reaction step, extraction step or oxidation reaction step.

EXAMPLES

Next, the present invention will be explained by referring to Examples, but the scope of the present invention is not limited by these ranges. Incidentally, a yield of the formed piperonal was calculated out in terms of mole.

Example 1

In a flat bottom separable flask having an inner volume of 7 liters, 500.0 g (4.09 mol) of 1,2-methylenedioxybenzene and 250 ml of 4-methyl-2-pentanone were charged under nitrogen atmosphere, and the mixture was cooled to −5° C. while stirring. Then, a mixture comprising 833.4 g (4.44 mol) of a 40% by weight aqueous glyoxylic acid solution and 857.8 g (8.40 mol) of 96% by weight sulfuric acid was gradually added dropwise, and then, the mixture was stirred at −5° C. for 21 hours.

Then, 3000 ml of 4-methyl-2-pentanone was added, and 1030.0 g (16.9 mol) of 28% by weight aqueous ammonia was gradually added to the mixture while maintaining the liquid temperature to −10 to 5° C. to effect neutralization. After the neutralization, the mixture was heated to 80° C., and 3,4-methylenedioxymandelic acid was extracted in a 4-methyl-2-pentanone layer (an organic solvent layer). At this time, the reaction mixture was separated into two layers of an organic solvent layer and an aqueous layer.

Then, the aqueous layer was removed, and the organic solvent layer was concentrated (2200 ml of 4-methyl-2-pentanone was removed). After concentration, the reaction mixture in a slurry state was transferred to a round bottom separable flask with an inner volume of 20 liters, and cooled to 10° C. while stirring under nitrogen atmosphere. Thereafter, 1746.7 g (2.78 mol) of 10% by weight nitric acid was gradually added dropwise, and the temperature of the mixture was raised to 50° C. and the mixture was stirred at the temperature for one hour.

After completion of the reaction, the mixture was cooled to 25° C., 140 ml (1.00 mol) of a 25% by weight aqueous sodium hydroxide solution was added to the mixture to make up the whole reaction mixture weak basic (pH=7.9). Subsequently, 4-methyl-2-pentanone layer (an organic solvent layer) and an aqueous layer were separated, and the organic solvent layer was analyzed by gas chromatography, then no 1,2-methylenedioxy-4-nitrobenzene which is a by-product was detected. Also, when it was analyzed by high performance liquid chromatography, a conversion of 1,2-methylenedioxybenzene was 97%, and a yield of piperonal was 78% (in terms of mole).

Example 2

In a flat bottom separable flask having an inner volume of 500 ml, 50.0 g (409.4 mmol) of 1,2-methylenedioxybenzene and 50 ml of acetic acid were charged under nitrogen atmosphere, and then, the mixture was cooled to 0° C. while stirring. Then, a mixture of 83.4 g (450.6 mmol) of a 40% by weight glyoxylic acid aqueous solution and 85.8 g (839.8 mmol) of 96% by weight sulfuric acid was gradually added dropwise, and then, the mixture was stirred at 5° C. for 21 hours.

Then, 200 ml of ethyl acetate was added to the mixture, and then, 102.0 g (1677 mmol) of 28% by weight aqueous ammonia was gradually added to the mixture while maintaining the liquid temperature to −10 to 5° C. to effect neutralization. After the neutralization, the mixture was heated to 60° C., and the 3,4-methylenedioxymandelic acid was extracted in an ethyl acetate layer (an organic solvent layer). At this time, the reaction mixture was separated into two layers of an organic solvent layer and an aqueous layer.

Then, the aqueous layer was removed, and the organic solvent layer was concentrated (ethyl acetate was completely removed by distillation), 173 ml of water and 160 ml of toluene were newly added to the concentrate, and the mixture was cooled to 0° C. while stirring under nitrogen atmosphere. Then, 33.9 g (328.2 mmol) of 61% by weight nitric acid was gradually added dropwise, and the temperature of the mixture was raised to 40° C., and the mixture was stirred at the temperature for one hour.

After completion of the reaction, the mixture was cooled to 0° C., 80 ml (0.57 mol) of a 25% by weight aqueous sodium hydroxide solution was added to the mixture to make up the whole reaction mixture weak basic (pH=7.9). Subsequently, the toluene layer and the aqueous layer were separated, and the toluene layer was analyzed by gas chromatography, no 1,2-methylenedioxy-4-nitrobenzene which is a by-product was detected. Also, when it was analyzed by high performance liquid chromatography, a conversion of 1,2-methylenedioxybenzene was 97%, and a yield of the piperonal was 80% (in terms of mole).

Utilizability in Industry

According to the present invention, a process for producing a high quality piperonal with high yield can be provided by completely inhibiting formation of 1,2-methylenedioxy-4-nitrobenzene, without taking out 3,4-methylenedioxymandelic acid which is an intermediate in the course of the reaction as a crystal, and carrying out from the above-mentioned addition reaction step to the oxidation reaction step continuously using 1,2-methylenedioxybenzene as a starting material.

What is claimed is:

1. A process for producing piperonal which comprises continuous three steps of:
    (A) an addition reaction step wherein 1,2-methylenedioxy-benzene and glyoxylic acid are reacted to form 3,4-methylenedioxymandelic acid in the presence of a strong acid,
    (B) an extraction step wherein an organic solvent is then added to a reaction mixture and the mixture is neutralized with a base to extract 3,4-methylenedioxymandelic acid in an organic solvent layer, and separating the organic solvent layer and an aqueous-layer, and
    (C) an oxidation reaction step wherein the aqueous layer is removed and the organic solvent layer is concentrated, and then, nitric acid is added to a concentrate, and the 3,4-methylenedioxymandelic acid and nitric acid are reacted to form piperonal.

2. The process for producing piperonal according to claim 1, wherein the strong acid is sulfuric acid.

3. The process for producing piperonal according to claim 1, wherein the addition reaction step is carried out at −20 to 10° C.

4. The process for producing piperonal according to claim 1, wherein 3,4-methylenedioxymandelic acid and nitric acid are reacted by newly adding a reaction solvent after concentrating the organic solvent layer in the oxidation reaction step.

5. The process for producing piperonal according to claim 1, wherein the organic solvent to be used in the extraction step is selected from the group consisting of ketones, organic acid esters, and ethers.

6. The process for producing piperonal according to claim 5, wherein the organic solvent to be used in the extraction step is at least one selected from the group consisting of acetone, 2-butanone, 3-pentanone, 2-pentanone, 4-methyl-2-pentanone, cyclopentanone, cyclohexanone, ethyl formate, isopropyl formate, butyl formate, methyl acetate, ethyl acetate, isopropyl acetate, butyl acetate, methyl propionate, ethyl propionate, isopropyl propionate, butyl propionate, diethyl ether, diisopropyl ether, dibutyl ether and tetrahydrofuran.

7. The process for producing piperonal according to claim 6, wherein the organic solvent to be used in the extraction step is selected from the group consisting of acetone, 2-butanone, 3-pentanone, 2-pentanone, 4-methyl-2-pentanone, cyclopentanone, and cyclohexanone.

8. The process for producing piperonal according to claim 1, wherein the base to be used in the extraction step is selected fro the group consisting of an aqueous alkali metal hydroxide solution and aqueous ammonia.

9. The process for producing piperonal according to claim 8, wherein the base to be used in the extraction step is selected from the group consisting of an aqueous sodium hydroxide solution, an aqueous potassium hydroxide solution and aqueous ammonia.

10. The process for producing piperonal according to claim 9, wherein the base to be used in the extraction step is 10 to 48% by weight of an aqueous alkali metal hydroxide solution or 5 to 28% by weight of aqueous ammonia.

11. The process for producing piperonal according to claim 1, wherein the extraction step is carried out at 40 to 80° C.

12. The process for producing piperonal according to claim 1, wherein the neutralization with a base is carried out at −20 to 50° C.

13. The process for producing piperonal according to claim 1, wherein the nitric acid is an aqueous solution of 5 to 70% by weight.

14. The process for producing piperonal according to claim 1, wherein an amount of the nitric acid to be used is 0.5 to 1.0 mole based on 1 mole of 1,2-methylenedioxybenzene.

15. The process for producing piperonal according claim 4, wherein an amount of the nitric acid to be used is 0.55 to 0.8 mole based on 1 mole of 1,2-methylenedioxybenzene.

* * * * *